United States Patent [19]
Tamura et al.

[11] Patent Number: 4,668,827
[45] Date of Patent: May 26, 1987

[54] PROCESS FOR PREPARING 2-(1-HYDROXYALKYL) CYCLOHEXANONE AND/OR 2-ALKYLIDENE CYCLOHEXANONE

[75] Inventors: Mitsuhiko Tamura; Haruo Katsumata; Kiyoharu Urakawa, all of Kita-Kyushu; Yoshiaki Ohtani, Nakama, all of Japan

[73] Assignee: Mitsubishi Chemical Industries Ltd., Tokyo, Japan

[21] Appl. No.: 825,787

[22] Filed: Feb. 4, 1986

Related U.S. Application Data

[63] Continuation of Ser. No. 650,499, Sep. 14, 1984, abandoned.

[30] Foreign Application Priority Data

Sep. 28, 1983 [JP] Japan ................................. 58-179986

[51] Int. Cl.$^4$ ............................................. C07C 45/75
[52] U.S. Cl. .................................................. 568/345
[58] Field of Search ............................... 568/345, 390

[56] References Cited

U.S. PATENT DOCUMENTS 2,519,327  8/1950  Wearn et al. ...................... 568/345
3,942,761  3/1976  Schleppnik ........................ 568/345

OTHER PUBLICATIONS

Nielsen et al., "Organic Reactions", vol. 16, pp. 38–43 (1968).

Primary Examiner—James H. Reamer
Attorney, Agent, or Firm—Oblon, Fisher, Spivak, McClelland & Maier

[57] ABSTRACT

The present invention relates to a process for preparing a 2-(1-hydroxyalkyl)cyclohexanone and/or a 2-alkylidene cyclohexanone. According to the present invention, the reaction of cyclohexanone with an aliphatic aldehyde is conducted in a heterogeneous system of an oil-in-water emulsion, whereby it is possible to obtain the 2-(1-hydroxyalkyl)cyclohexanone and/or the 2-alkylidene cyclohexanone in high selectivity.

8 Claims, No Drawings

PROCESS FOR PREPARING 2-(1-HYDROXYALKYL) CYCLOHEXANONE AND/OR 2-ALKYLIDENE CYCLOHEXANONE

This application is a continuation of application Ser. No. 650,499, filed Sept. 14, 1984, now abandoned.

The present invention relates to a process for preparing a 2-(1-hydroxyalkyl)cyclohexanone (hereinafter sometimes referred to simply as "hydroxyalkylcyclohexanone") and/or a 2-alkylidene cyclohexanone (hereinafter sometimes referred to simply as "alkylidene cyclohexanone"). More particularly, the present invention relates to a process for preparing a hydroxyalkyl cyclohexanone and/or an alkylidene cyclohexanone in good yield by controlling the formation of by-products by conducting the reaction of cyclohexanone with an aliphatic aldehyde under a certain specific condition.

The hydroxyalkyl cyclohexanone and the alkylidene cyclohexanone are useful as intermediates in the field of organic chemistry. For instance, 2-(1-hydroxy-isobutyl) cyclohexanone and 2-isobutylidene cyclohexanone are useful as starting materials for the production of 2,3-dihydro-2,2-dimethyl-7-hydroxybenzofuran which is important as an intermediate for 2,3-dihydro-2,2-dimethyl-7-benzofuranyl methycarbamate which is an insecticidal agent having a wide spectrum and being known by the common name of carbofuran (published European patent application No. 90976).

Heretofore, various processes have been proposed for the preparation of a 2-(1-hydroxyalkyl)cyclohexanone and/or a 2-alkylidene cyclohexanone. For instance, the following reactions have been known for the preparation of the 2-(1-hydroxyalkyl)cyclohexanone.

(i) MUKAIYAMA et al., J. Am. Chem. Soc. 96, 7503 (1974)

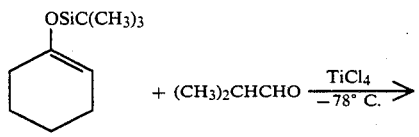

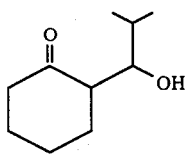

(ii) NOZAKI et al., Bull. Chem. Soc. Jap. 53, 3301 (1980)

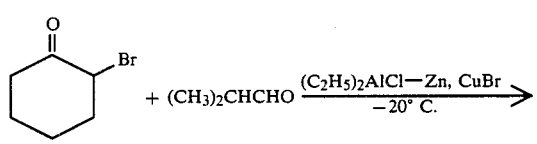

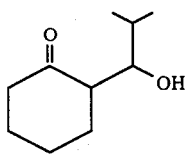

However, these reactions are not practically very useful since they require special reagents, or they are conducted at an extremely low temperature.

Further, Chemical Abstracts 57, 11042e discloses a process for preparing 2-isobutylidene cyclohexanone by subjecting cyclohexanone and isobutyl aldehyde to aldol condensation and dehydration in the presence of an alkali in a homogeneous reaction system using an alcohol as the solvent. However, this process has a drawback that the yield is as low as 41%.

Thus, no process which has been proposed is fully satisfactory.

Under the circumstances, the present inventors have conducted extensive research for the preparation of the 2-(1-hydroxyalkyl)cyclohexanone and/or the 2-alkylidene cyclohexanone, and have found it possible to remarkably improve the selectivity for the desired product and to suppress the formation of highly condensed products as by-products by conducting the aldol condensation of cyclohexanone and an aliphatic aldehyde and/or the dehydration reaction of the resultant hydroxyalkyl cyclohexanone in a heterogeneous system of an oil-in-water emulsion.

Thus, the present invention provides a process for preparing a 2-(1-hydroxyalkyl)cyclohexanone represented by the formula:

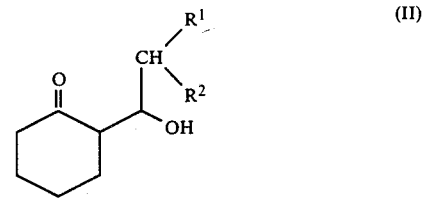

where each of $R^1$ and $R^2$, which may be the same or different, is a hydrogen atom or an alkyl group having 1 or 2 carbon atoms, or a 2-alkylidene cyclohexanone represented by the formula:

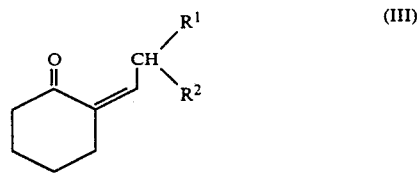

where $R^1$ and $R^2$ are as defined above, which comprises reacting cyclohexanone with an aliphatic aldehyde represented by the formula:

where $R^1$ and $R^2$ are as defined above, in the presence of an alkali, in a heterogeneous system of an oil-in-water emulsion obtained by mixing water with cyclohexanone and an aliphatic aldehyde so that said emulsion comprises 1 part by weight of an organic phase composed essentially of the cyclohexanone and the aliphatic aldehyde and from 0.5 to 20 parts by weight of an aqueous phase containing the alkali.

Now, the present invention will be described in detail with reference to the preferred embodiments.

The reaction of the present invention, i.e. the reaction wherein the aliphatic aldehyde of the formula I is added to cyclohexanone to form the 2-(1-hydroxyalkyl) cyclohexanone of the formula II, is so-called aldol condensation. Therefore, we call the reaction "condensation or condensation reaction" in the specification, although addition reaction is correct.

As specific examples of the aliphatic aldehyde of the formula I as the starting material for the process of the present invention, there may be mentioned acetoaldehyde, propionaldehyde, n-butyl aldehyde, isobutyl aldehyde and 2-ethylbutyl aldehyde. Isobutyl aldehyde and n-butyl aldehyde are particularly preferred.

On the other hand, the hydroxyalkyl cyclohexanone of the formula II and/or the alkylidene cyclohexanone of the formula III obtained by the present invention includes various compounds depending upon the starting material aliphatic aldehyde of the formula I. As specific examples of the hydroxyalkyl cyclohexanone, there may be mentioned 2-(1-hydroxyethyl)cyclohexanone, 2-(1-hydroxypropyl)cyclohexanone, 2-(1-hydroxybutyl) cyclohexanone, 2-(1-hydroxyisobutyl)cyclohexanone and 2-(1-hydroxy-2-ethylbutyl)cyclohexanone. Particularly preferred are 2-(1-hydroxybutyl)cyclohexanone and 2-(1-hydroxyisobutyl)cyclohexanone.

As specific examples of the alkylidene cyclohexanone, there may be mentioned 2-ethylidene cyclohexanone, 2-propylidene cyclohexanone, 2-butylidene cyclohexanone, 2-isobutylidene cyclohexanone and 2-(2-ethylbutylidene) cyclohexanone. Particularly preferred are 2-butylidene cyclohexanone and 2-isobutylidene cyclohexanone.

The molar ratio of the aliphatic aldehyde to cyclohexanone in the condensation reaction of the present invention is 0.05–0.8:1, preferably 0.1–0.7:1, more preferably 0.2–0.6:1. The reaction can of course be conducted outside these ranges. However, if the molar ratio of the aliphatic aldehyde to the cyclohexanone becomes big, by-products such as 2,6-bis(1-hydroxyalkyl)cyclohexanone and/or 2,6-dialkylidene cyclohexanone increase and the selectivity for the desired product lowers, such being undesirable. The mixture of cyclohexanone and the aliphatic aldehyde constitutes an organic phase, whereby an excess amount of cyclohexanone serves as a solvent, and accordingly no special organic solvent is required for the condensation reaction.

In the condensation and dehydration reactions of the present invention, an aqueous phase containing an alkali is present in the reaction system so that the reaction system becomes an emulsion, and the reaction is conducted in a heterogeneous system.

As the alkali serving as a catalyst, hydroxide, carbonate or bicarbonate of an alkali metal can effectively be used. It is also possible to use an alkaline earth metal hydroxide. Particularly preferred is an alkali metal hydroxide. Normally the alkali is present in an amount of from 0.1 to 10 mols relative to 1 mol of the aliphatic aldehyde. The alkali concentration in the aqueous phase is usually from 1 to 10% by weight, preferably from 2 to 7% by weight.

In the present invention, the weight ratio of the aqueous phase to the organic phase is referred to as the aqueous phase ratio. When the aqueous phase ratio is from 0.5 to 20, the reaction system usually becomes an oil-in-water type emulsion, and it is thereby possible to conduct the heterogeneous reaction of the present invention. The aqueous phase ratio is preferably from 1 to 10, more preferably from 2 to 8. The greater the aqueous phase ratio is, the greater the reaction velocities of the condensation and dehydration reactions become, and accordingly the better the selectivity for the desired product. The reason for the increase of the reaction velocities when the aqueous phase ratio is made large, is believed to be as follows.

Namely, the reaction of the present invention is a reaction in a heterogeneous system comprising an aqueous phase and the organic phase, and accordingly as water increases, the reaction system tends to be an oil-in-water type emulsion, whereby the contact surface area at the interface increases, and the reaction velocities become high.

However, if the aqueous phase ratio is too large, it will be difficult to separate the liquid layer from the aqueous layer to isolate the desired product after the reaction, or the desired product tends to be dissolved in the aqueous phase, such being undesirable. On the other hand, if the aqueous phase ratio is too small, the reaction system becomes a water-in-oil type emulsion, whereby the yield of the desired product lowers, such being undesirable. In the heterogeneous system reaction of the present invention, the yield of the desired product is believed to be delicately affected by the partition coefficients of e.g. the starting material aldehyde, the desired product and the by-products to the organic and aqueous phases of the reaction system.

The reaction temperature is selected within a range of not higher than 150° C. If the reaction is conducted at a relatively low temperature, the hydroxyalkyl cyclohexanone is obtained by the condensation of cyclohexanone with the aliphatic aldehyde, while if the reaction is conducted at a relatively high temperature, the condensation and the dehydration take place in a single step, whereby the alkylidene cyclohexanone is obtained. In order to obtain the hydroxyalkyl cyclohexanone as the major component product, the reaction temperature is usually less than 50° C., preferably from 0° to less than 50° C., more preferably from 5° to 40° C. If the reaction temperature is too low, the reaction rate will be too slow to be practically useful.

On the other hand, in order to obtain the alkylidene cyclohexanone as the major component product by the single step of condensation and dehydration, the reaction temperature is usually from 50° to 150° C., preferably from 70° to 100° C., more preferably from 75° to 96° C. (i.e. the azeotropic boiling point of a mixture of water and cyclohexanone). The greater the temperature, the higher the reaction rate. However, as the temperature rises, the amount of the by-products such as a 2,6-dialkylidene cyclohexanone, tends to increase. Further, if the aqueous phase ratio is too large at the high temperature, the amount of the by-product i.e. the 2,6-dialkylidene cyclohexanone increases. Accordingly, in the heterogeneous system reaction of the present invention, it is necessary to select a proper reaction condition taking into consideration of the overall effects of the reaction temperature and the aqueous phase ratio.

The reaction time is optionally determined taking into accounts the molar ratio of the aliphatic aldehyde to cyclohexanone, the aqueous phase ratio, the alkali concentration and the reaction temperature and depending upon the desired product. The reaction time is usually from 30 minutes to 6 hours. In the case where only the condensation reaction is to be conducted at a relatively low temperature, the reaction time is preferably adjusted within a range of from 1 to 5 hours. Whereas, in the case where the condensation and dehydration are conducted in a single step at a relatively high temperature, it is industrially preferred to adjust the reaction temperature within a range of from 1 to 3 hours.

The reaction of the present invention is a heterogeneous system reaction, and accordingly in order to increase the reaction rate, it is important to increase the contact surface area. Inadequate agitation where the organic layer and the aqueous layer are present independently, i.e. the state where the aqueous layer and the organic layer are separated each other, is not desirable. Accordingly, it is necessary to conduct adequate agitation so that the entire reaction system becomes a uniform oil-in-water type emulsion.

After the reaction, the desired product is recovered in accordance with a conventional chemical technique. For instance, the reaction mixture is left to form two layers of water phase and organic phase, whereupon the organic layer is separated from the aqueous layer, and the desired product is recovered from the organic layer. The temperature for the separation is at a level of the above-mentioned reaction temperature. Prior to the separation of the organic layer and the aqueous layer, the reaction mixture may be neutralized by an addition of an inorganic acid such as hydrochloric acid, and an organic acid such as acetic acid, citric acid, tartaric acid, phthalic acid or oxalic acid. However, in such a case, the aqueous layer after the neutralization is disposed, and the desired product is recovered from the organic layer by distillation.

On the other hand, when the neutralization is conducted after the separation, only the organic phase may be neutralized by an optional acid, preferably acetic acid, citric acid, tartaric acid, phthalic acid or oxalic acid, by which the control of the pH can readily be conducted. In this case, the aqueous layer may be disposed, or may be reused by recycling it as the aqueous phase source for the heterogeneous system reaction. Such recycling is industrially advantageous.

The organic phase after the neutralization contains a hydroxyalkyl cyclohexanone and/or an alkylidene cyclohexanone, unreacted cyclohexanone, high boiling by-products such as 2,6-bis(1-hydroxyalkyl)cyclohexanone and/or 2,6-dialkylidene cyclohexanone, depending upon the reaction temperature, as well as from 4 to 5% of water. Such an organic phase is first subjected to distillation to recover cyclohexanone, and then the residual mixture is subjected to rectification, whereby the desired product is separated from the high boiling by-products and recovered.

The distillation is conducted under atmospheric pressure or reduced pressure, preferably under reduced pressure of from 1 to 100 mmHg. Water contained in the organic phase is azeotropically distilled together with cyclohexanone, and the recovered cyclohexanone can be supplied as it is to the reaction of the present invention. By the above distillation operation, cyclohexanone, the hydroxyalkyl cyclohexanone, the alkylidene cyclohexanone and the high boiling by-products can be separated relatively easily, whereby the desired product having a purity of at least 98% can be obtained.

According to the present invention, by the heterogeneous system reaction employing an aqueous alkali solution, it is not required to use special organic solvents or special reactants, and it is possible to obtain the desired product in a simple operation and in good selectivity. Further, by properly selecting the water phase ratio, the molar ratio of the aliphatic aldehyde to cyclohexanone, the reaction temperature and the like, it is possible to attain the selectivity for the desired product as high as 80%, more than 90% as the case may be, based on the aliphatic aldehyde and/or cyclohexanone.

Further, the reaction rate of the aliphatic aldehyde is high, whereby the recovery step for the aliphatic aldehyde can be omitted. Namely, it is possible to obtain the hydroxyalkyl cyclohexanone and/or alkylidene cyclohexanone industrially advantageously, simply by recovering and recycling cyclohexanone which is used in an excess amount.

Now, the present invention will be described in further detail with reference to Examples. However, it should be understood that the present invention is by no means restricted to these specific Examples.

EXAMPLE 1

Into a 1 liter separatory flask equipped with a jacket and provided with a stirrer, a reflux condenser, a thermometer and a dropping funnel, 767 ml of an aqueous sodium hydroxide solution having a concentration of 2.5% by weight was fed. The internal temperature was raised to 90° C., and 192 g of a mixture of isobutyl aldehyde (hereinafter referred to simply as "IBD") and cyclohexanone (hereinafter referred to simply as "CHN") (IBD/CHN molar ratio: 0.3) was fed into the flask in a short period of time, and this was taken as the initiation point of the reaction. After the reaction was continued for 1 hour under adequate stirring, the reaction mixture was permitted to stand and the organic layer was separated from the aqueous layer. The organic phase and the aqueous phase were analyzed, respectively. The results are shown in Table 1.

The analyses were conducted as follows:

Orqanic phase:

An amount of the organic phase within a range of from 0.2 to 0.25 g was accurately weighed and put into a 10 ml measuring flask, and an ethanol solution containing 40 mg of n-heptanol as an internal standard substance was added. Then, a few small pieces of dry ice were added for neutralization. Then, ethanol was added to bring the total volume to 10 ml.

Aqueous phase:

About 20 g of the aqueous phase was accurately weighed and put into a 25 ml measuring flask, and an ethanol solution containing 40 mg of n-heptanol as an internal standard substance was added. Then, dilute hydrochloric acid was added to adjust the pH to 7, and the total volume was adjusted to 25 ml.

Analysis:

The organic phase and the aqueous phase prepared by the above-mentioned procedure were respectively analyzed by gas chromatography under the following conditions.

Column: : PEG 20M (10%)
Column temperature : 50°–200° C. 4° C./min
Detector temperature: 250° C.
Carrier gas : 80 ml/min-$N_2$
Hydrogen : 0.6 kg/$cm^2$G
Air : 1.0 kg/$cm^2$G In Table 1, BCHN represents 2-isobutylidene cyclohexanone, and DBCHN represents 2,6-diisobutylidene cyclohexanone.

EXAMPLES 2 to 10

The reaction was conducted in the same manner as in Example 1 except that the conditions such as the aldehyde/CHN molar ratio, the aqueous phase ratio (weight ratio), the concentration of the aqueous alkali solution (% by weight), the temperature and/or the reaction time were replaced by the conditions described in Table 1. The results thereby obtained are shown in Table 1.

EXAMPLE 11

The reaction was conducted in the same manner as in Example 2 except that n-butyl aldehyde was used instead of isobutyl aldehyde. The results are shown in Table 1. However, in Table 1, so far as Example 11 is concerned, BCHN represents 2-n-butylidene cyclohexanone, and DBCHN represents 2,6-di-n-butylidene cyclohexanone.

COMPARATIVE EXAMPLE 1

The reaction was conducted in the same manner as in Example 2 except that the aqueous phase ratio was changed to 0.2 i.e. outside the range of the present invention. The results are shown in Table 1, and the selectivity for 2-isobutylidene cyclohexanone was as low as less than 50%.

2.5% by weight was fed. The internal temperature was maintained at 40° C., and 192 g of a mixture of isobutyl aldehyde and cyclohexanone (IBD/CHN molar ratio: 0.3) was fed into the flask in a short period of time and this was taken as the initiation point of the reaction. After the reaction was continued for 1 hour under adequate stirring, the reaction mixture was permitted to stand and the organic layer was separated from the aqueous layer. The organic phase and the aqueous phase were respectively analyzed to obtain the results shown in Table 2. The analyses were conducted in the same manner as in Example 1.

In Table 2, HBCHN represents 2-(1-hydroxyisobutyl) cyclohexanone, and BCHN represent 2-isobutylidene cyclohexanone.

EXAMPLES 13 to 16

The reactions were conducted in the same manner as in Example 12 except that the conditions such as the aldehyde/CHN molar ratio, the aqueous phase ratio (weight ratio), the temperature and/or the reaction time were replaced the conditions described in Table 2. The results are shown in Table 2.

EXAMPLE 17

The reaction was conducted in the same manner as in Example 12 except that n-butyl aldehyde was used instead of isobutyl aldehyde, and the reaction temperature was adjusted to 30° C. The results are shown in Table 2. However, in Table 2, so far as Example 17 is concerned, HBCHN represents 2-(1-hydroxy-n-butyl) cyclohexanone, and BCHN represent 2-n-butylidene cyclohexanone.

TABLE 1

| | Reaction conditions | | | | | Results of the reaction | | | | |
|---|---|---|---|---|---|---|---|---|---|---|
| | Aldehyde/ CHN (molar | Aqueous phase ratio (weight | Concentration of an aqueous alkali solution | Temp. | Time | Remaining aldehyde | Selectivity (%) based on aldehyde | | Selectivity (%) based on CHN | |
| No. | ratio) | ratio) | (% by weight) | (°C.) | (hr.) | (molar %) | BCHN | DBCHN | BCHN | DBCHN |
| Example 1 | 0.3 | 4.0 | 2.5 | 90 | 1.0 | 0.6 | 91.2 | 4.1 | 91.3 | 2.0 |
| Example 2 | 0.3 | 4.0 | 2.5 | 80 | 1.0 | 2.1 | 93.2 | 3.5 | 92.7 | 2.3 |
| Example 3 | 0.3 | 4.0 | 2.5 | 70 | 1.0 | 3.2 | 80.9 | 2.3 | 83.4 | 1.2 |
| Example 4 | 0.3 | 4.0 | 2.5 | 70 | 3.0 | 0.6 | 94.1 | 4.7 | 96.2 | 2.4 |
| Example 5 | 0.3 | 2.0 | 2.5 | 80 | 1.0 | 3.3 | 85.5 | 5.0 | 79.9 | 2.2 |
| Example 6 | 0.3 | 8.0 | 2.5 | 80 | 1.0 | 0.4 | 93.7 | 4.9 | 92.1 | 2.2 |
| Example 7 | 0.1 | 4.0 | 2.5 | 80 | 1.0 | 0.1 | 97.9 | 2.0 | 99.0 | 1.0 |
| Example 8 | 0.6 | 4.0 | 2.5 | 80 | 1.0 | 3.1 | 86.9 | 6.0 | 90.6 | 3.4 |
| Example 9 | 0.8 | 4.0 | 2.5 | 80 | 1.0 | 5.4 | 82.2 | 8.0 | 88.8 | 6.5 |
| Example 10 | 0.3 | 4.0 | 5.0 | 80 | 1.0 | 0.6 | 93.5 | 3.5 | 94.9 | 1.8 |
| Example 11 | 0.3 | 4.0 | 2.5 | 80 | 1.0 | 2.5 | 92.8 | 3.5 | 91.5 | 1.9 |
| Comparative Example 1 | 0.3 | 0.2 | 2.5 | 80 | 1.0 | 10.5 | 47.4 | 3.7 | 45.8 | 1.7 |

EXAMPLE 12

Into a 1 liter separatory flask equpped with a jacket and provided with a stirrer, a reflux condenseer, a thermometer and a dropping funnel, 767 ml of an aqueous sodium hydroxide solution having concentration of

TABLE 2

| | Reaction conditions | | | | | Results of the reaction | | | | | |
|---|---|---|---|---|---|---|---|---|---|---|---|
| | Aldehyde/ CHN (molar | Aqueous phase ratio (weight | Concentration of an aqueous alkali solution | Temp. | Time | Remaining aldehyde (molar | Selectivity (%) based on aldehyde | | Di- | Selectivity (%) based on CHN | | Di- |
| No. | ratio) | ratio) | (% by weight) | (°C.) | (hr) | %) | HBCHN | BCHN | adduct* | HBCHN | BCHN | adduct* |
| Example 12 | 0.3 | 4.0 | 2.5 | 40 | 1.0 | 3.6 | 87.8 | 3.8 | 0.7 | 92.4 | 4.0 | 0.4 |
| Example 13 | 0.3 | 4.0 | 2.5 | 30 | 1.0 | 6.9 | 89.6 | 1.7 | 0.3 | 95.4 | 1.8 | 0.1 |
| Example 14 | 0.3 | 4.0 | 2.5 | 20 | 5.0 | 2.5 | 88.3 | 2.6 | 0.5 | 93.8 | 2.8 | 0.3 |
| Example 15 | 0.1 | 4.0 | 2.5 | 30 | 1.0 | 4.2 | 91.7 | 1.4 | 0.1 | 96.1 | 1.4 | 0.1 |
| Example 16 | 0.3 | 8.0 | 2.5 | 30 | 1.0 | 3.0 | 86.6 | 4.9 | 1.1 | 91.5 | 5.2 | 0.6 |
| Exam- | 0.3 | 4.0 | 2.5 | 30 | 1.0 | 3.7 | 86.7 | 3.4 | 0.8 | 93.0 | 3.6 | 0.4 |

TABLE 2-continued

| | Reaction conditions | | | | | | Results of the reaction | | | | | |
|---|---|---|---|---|---|---|---|---|---|---|---|---|
| | Aldehyde/ CHN | Aqueous phase ratio | Concentration of an aqueous | Temp. | Time | Re- maining aldehyde | Selectivity (%) based on aldehyde | | | Selectivity (%) based on CHN | | |
| | | | | | | | Mono-adduct | | Di- | Mono-adduct | | Di- |
| No. | (molar ratio) | (weight ratio) | alkali solution (% by weight) | (°C.) | (hr) | (molar %) | HBCHN | BCHN | adduct* | HBCHN | BCHN | adduct* |
| ple 17 | | | | | | | | | | | | |

*Di-adduct represents the corresponding 2,6-bis(1-hydroxyalkyl)cyclohexanone and 2,6-dialkylidene cyclohexanone.

We claim:

1. A process for preparing a 2-alkylidene cyclohexanone represented by the formula:

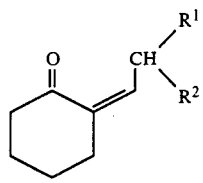

(III)

wherein each of $R^1$ and $R^2$, which may be the same or different, is a hydrogen atom or an alkyl group having 1 or 2 carbon atoms, which comprises:
reacting cyclohexanone with an aliphatic aldehyde represented by the formula:

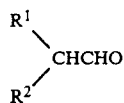

(I)

wherein $R^1$ and $R^2$ each are as defined above, in the presence of an alkali, in a heterogeneous system of an oil-in-water emulsion obtained by mixing water with cyclohexanone and an aliphatic aldehyde so that said emulsion comprises 1 part by weight of an organic phase composed essentially of the cyclohexanone and the aliphatic aldehyde and from 1 to 10 parts by weight of an aqueous phase containing the alkali at a temperature of from 75° to 150° C.

2. The process according to claim 1, wherein the reaction temperature ranges from 75° to 100° C.

3. The process according to claim 1, wherein the aliphatic aldehyde is isobutyl aldehyde or n-butyl aldehyde.

4. The process according the claim 1, wherein the aliphatic aldehyde is isobutyl aldehyde.

5. The process according to claim 1, wherein from 0.05 to 0.8 mol of the aliphatic aldehyde is used relative to 1 mol of cyclohexanone.

6. The porcess according to claim 5, wherein from 0.1-0.7 moles of aliphatic aldehyde is reacted with 1 mole of cyclohexanone.

7. The process according to claim 1, wherein from 0.1 to 10 mols of the alkali is present relative to 1 mol of the aliphatic aldehyde.

8. The process according to claim 1, wherein the alkali concentration in the aqueous phase is from 1 to 10% by weight.

* * * * *